United States Patent
Li et al.

(10) Patent No.: US 11,864,994 B2
(45) Date of Patent: Jan. 9, 2024

(54) SEPARATELY RELEASABLE AORTIC VALVE STENT

(71) Applicant: NINGBO JENSCARE BIOTECHNOLOGY CO., LTD., Zhejiang (CN)

(72) Inventors: Yibin Li, Ningbo (CN); Linghe Zheng, Ningbo (CN); Shiwen Lv, Ningbo (CN)

(73) Assignee: JENSCARE SCIENTIFIC CO., LTD., Zhejiang (CN)

( * ) Notice: Subject to any disclaimer, the term of this patent is extended or adjusted under 35 U.S.C. 154(b) by 131 days.

(21) Appl. No.: 17/312,733

(22) PCT Filed: Nov. 28, 2019

(86) PCT No.: PCT/CN2019/121427
§ 371 (c)(1),
(2) Date: Jun. 10, 2021

(87) PCT Pub. No.: WO2020/119462
PCT Pub. Date: Jun. 18, 2020

(65) Prior Publication Data
US 2022/0015898 A1    Jan. 20, 2022

(30) Foreign Application Priority Data
Dec. 14, 2018   (CN) .......................... 201811530921.3

(51) Int. Cl.
*A61F 2/24*   (2006.01)

(52) U.S. Cl.
CPC .......... *A61F 2/2418* (2013.01); *A61F 2/2436* (2013.01); *A61F 2220/0075* (2013.01); *A61F 2220/0083* (2013.01)

(58) Field of Classification Search
CPC .................. A61F 2/2418; A61F 2/2436; A61F 2220/0075; A61F 2220/0083;
(Continued)

(56) References Cited

U.S. PATENT DOCUMENTS

2007/0213812 A1* 9/2007 Webler .................. A61F 2/2451
623/2.37
2016/0158007 A1* 6/2016 Centola ................. A61F 2/2418
623/2.11
(Continued)

FOREIGN PATENT DOCUMENTS

CN   101951857   1/2011
CN   104918583   9/2015
(Continued)

OTHER PUBLICATIONS

International Search Report issued for International Patent Application No. PCT/CN2019/121427, dated Feb. 21, 2020, 12 pages including English translation.

*Primary Examiner* — Megan Y Wolf
*Assistant Examiner* — Yasniary De La Caridad Morales
(74) *Attorney, Agent, or Firm* — Hamre, Schumann, Mueller & Larson, P.C.

(57) ABSTRACT

The present application relates to a separately releasable aortic valve stent, which includes a valve sewing segment, a positioning member, and a prosthetic valve. The prosthetic valve is connected to the valve sewing segment. The valve sewing segment and the positioning member are two independent components and connected to each other via a guiding device. The positioning member is able to be released prior to the valve sewing segment. A slide connection structure is disposed on the valve sewing segment. One end of the guiding device is connected to the positioning member, and another end of the guiding device passed through the slide connection structure is connected to the positioning member. The valve sewing segment is slidable along the guiding device.

17 Claims, 10 Drawing Sheets

(58) Field of Classification Search
CPC .......... A61F 2002/828; A61F 2250/006; A61F 2/2409; A61F 2/2412
See application file for complete search history.

(56) References Cited

U.S. PATENT DOCUMENTS

2017/0281345 A1* 10/2017 Yang ..................... A61F 2/2418
2019/0254819 A1* 8/2019 Hoffer ....................... A61F 2/95

FOREIGN PATENT DOCUMENTS

| | | |
|---|---|---|
| CN | 105208973 | 12/2015 |
| CN | 204951236 U | 1/2016 |
| CN | 105496607 | 4/2016 |
| CN | 105658180 | 6/2016 |
| CN | 105662652 | 6/2016 |
| CN | 106073946 | 11/2016 |
| CN | 107205822 | 9/2017 |
| CN | 108430393 | 8/2018 |
| CN | 109350311 | 2/2019 |
| CN | 109498215 | 3/2019 |
| CN | 209332385 U | 9/2019 |
| CN | 209548145 U | 10/2019 |
| EP | 3311779 | 4/2018 |

\* cited by examiner

SEPARATELY RELEASABLE AORTIC VALVE STENT

CROSS-REFERENCE TO RELATED APPLICATION

This application claims priority from China Patent Application No. 201811530921.3, entitled "SEPARATELY RELEASABLE AORTIC VALVE STENT", filed on Dec. 14, 2018, the entirety of which is incorporated by reference herein. This application is a national phase under 35 U.S.C. § 120 of international patent application PCT/CN2019/121427, entitled "SEPARATELY RELEASABLE AORTIC VALVE STENT" filed on Nov. 28, 2019, the content of which is also hereby incorporated by reference.

FIELD

The present application relates to the field of medical apparatus, and particularly to a separately releasable aortic valve stent.

BACKGROUND

The aortic valve stenosis is mainly caused by the sequela of the rheumatic fever, the congenital structural abnormality of the aortic valve, or the senile calcification of the aortic valve. Patients are asymptomatic during the compensatory period. Most patients with severe aortic valve stenosis have symptoms of fatigue, dyspnea (exertional or paroxysmal), angina pectoris, dizziness, or syncope, or even sudden death.

When the ventricle contracts, the aortic valve is open and the blood in the left ventricle flows into the aorta and toward the whole body. When the ventricle relaxes, the aortic valve is closed to prevent the blood in the aorta from flowing back into the left ventricle. The aortic regurgitation refers to the backward flow of the blood from the aorta into the left ventricle caused by incompetent closure of the aortic valve during the diastole due to the aortic insufficiency.

The valve replacement surgery is a traditional and effective treatment for the aortic valve diseases. However, many patients with such diseases are of advanced age, and have diseases associated with multiple organs. It is difficult for them to undergo the surgery considering their physical conditions, and these patients become hopeless patients for clinical treatment. In addition, the etiologies of the degenerative aortic valve diseases are still not well understood. Therefore, the etiological treatments cannot be performed. There is still no effective method for limiting the development of the degenerative aortic valve diseases, and the effects of the drug treatments are not ideal. The ideal treatments of aortic valve diseases should improve both the symptoms and the life span of the patients. The percutaneous balloon aortic valvuloplasty developed in early years has been used to treat the aortic valve stenosis. However, poor long-term effects are found in both single-center data and multiple-center registration data. In China, the valve replacement surgery is still a major treatment option. In recent years, some domestic and foreign researchers have carried out the basic and clinical studies of percutaneous aortic valve replacement, and have made some breakthrough progresses, providing an effective treatment for high-risk elderly patients with the aortic valve degeneration and requiring the valve replacement surgery. In 2002, Cribier et al. successfully performed a transcatheter aortic valve replacement (TAVR). To date, more than 50,000 TAVR procedures have been performed worldwide, and studies around the world have shown that this technique is safe and effective for the patients unable to undergo the valve replacement surgery or at high risk in the valve replacement surgery. Although most of the patients who underwent the TAVR were high risk patients, survival rates of them were higher than 90% at 30 days after the TAVR, and hemodynamic parameters of the patients were significantly improved after the TAVR.

However, at present, the autologous aortic valve insufficiency is still regarded as the contraindication of the TAVR, considering the following main reasons. The accurate positioning and correct release of the valve stent are most critical technical points in the TAVR. The right and left coronary artery ostia are located above the aortic valve, and the mitral valve is adjacent to and located below the aortic valve. If the positioning and the release are inaccurate, the lethal complications such as the blockage in the coronary arteries or the severe mitral regurgitation may occur. The traditional TAVR apparatus, both the SAPIEN and the CoreValve, are mainly used for the patients with the severe aortic valve stenosis but not the aortic regurgitation. In the traditional technology, some consensuses have been reached for the design of the apparatus for the patients with the aortic regurgitation. For example, the JenaValve and the Acurate abroad and the J-Valve in China all adopt the structure like an autologous valve clamp to position the three aortic sinuses, which is favorable to implanting the stent at the accurate position. However, the above current apparatus are mostly implanted via a heart apex path, not technically implanted percutaneously, and thus leads to a relatively large wound for the patients. The researchers and engineers in China have made some conceptual attempts to deal with the problem of too large sheath while taking the autologous valve clamp into account.

The patents CN201520325599.6 and CN201511017536.5 describe a dual ring aortic valve stent, including a main frame and an additional W-shaped annular fixing ring. Three feet of the fixing ring are configured to be fixed into the three aortic sinuses. The annular fixing ring is connected to the main frame via three nickel-titanium wires. The nickel-titanium wires are V-shaped, and the V-shaped bending portions thereof are corresponding to the V-shaped bending portions of the fixing ring. The V-shaped nickel-titanium wires can be stretched into the linear shape, so that the relative position between the fixing ring and the frame changes from an inner-outer relationship to an upper-lower relationship. This design has the following main problems. 1) After the annular fixing ring is released, it is difficult to manipulate the annular fixing ring to be aligned with the aortic sinuses, so that the adjustability is poor. 2) The annular fixing ring is stuck at the valve sinuses once it is released from the sheath and cannot be re-installed into the sheath, so that there is a high operational risk. 3) The annular fixing ring is provided with no limiting member, is therefore easy to bounce in the transport sheath, and cannot be completely aligned with the autologous valve after it is bounced out, increasing the adjusting difficulty. 4) When the valve is completely released, the autologous valve still has the risk of abutting against the aortic sinus wall and thus blocking the coronary arteries. 5) The upper and lower frames are difficult to be coaxially moved, and the malposition and interference are easy to occur.

The patent CN201610029112.9 describes a transcatheter aortic valve device. Similar to the above described structure, the upper end of the main frame forms a three-piece type upward horn structure. The lower side of the main frame is further provided with a position-limiting loop connected to the main frame via position-limiting wires. This design has the following problems. 1) After the release, the position-limiting loop is difficult to be operated to be aligned with the aortic sinuses, so the adjustability is poor. 2) Even the position-limiting loop is aligned with the aortic sinuses, due to the impact of the blood current, the position-limiting loop is easy to be rushed out from the sinuses, causing the ends of position-limiting loop unable to abut against the bottom of the aortic sinuses. 3) When the valve is completely released, a risk that the autologous valve leaflets abut against the aortic sinus wall and block the coronary arteries is still existed. 4) The upper and lower frames are difficult to be coaxially moved, and the malposition and interference are easy to occur.

In view of the above, the traditional technology can reduce the size of the delivery sheath while taking the autologous valve leaflets clamping member into account. However, in the traditional technology, the release of the position-limiting loop is uncontrollable, the concentricity of the position-limiting loop is poor, and the position-limiting loop is difficult to be adjusted and fixed. Moreover, there is the risk that the autologous valve leaflets block the coronary arteries. Thus, there is a need to provide a valve replacement device to address the above-described problem.

SUMMARY

An object of the present application is to overcome the restriction in the traditional technology and develop a novel separately releasable aortic valve stent to address the problem that the traditional separately releasable aortic valve stent cannot effectively control the position of the main frame and the positioning member, cannot effectively prevent the blockage of the coronary arteries, and cannot allow the completely released clamping member to be re-loaded into the sheath.

The object of the present application can be achieved by the following technical solutions.

A separately releasable aortic valve stent includes a valve sewing segment, a positioning member, and a prosthetic valve. The prosthetic valve is connected to the valve sewing segment. The valve sewing segment and the positioning member are two independent components and connected to each other via a guiding device. The positioning member is able to be released prior to the valve sewing segment. A slide connection structure is disposed on the valve sewing segment. One end of the guiding device is connected to the positioning member, and another end of the guiding device passed through the slide connection structure and is connected to the positioning member. The valve sewing segment is slidable along the guiding device.

The object of the present application can be further achieved by the following technical solutions.

In an embodiment, the positioning member includes an anchoring segment and a clamping segment connected to the anchoring segment. One end of the guiding device is connected to the clamping segment, and another end of the guiding device passed through the slide connection structure is connected to the anchoring segment. The valve sewing segment is slidable along the guiding device via the slide connection structure.

In an embodiment, the clamping segment is located at a proximal end of the anchoring segment, and integrated with the anchoring segment.

In an embodiment, the anchoring segment has a mesh structure or a wavy structure. In an embodiment, a surface of the anchoring segment is coated with a film or a fabric.

In an embodiment, the clamping segment has three claws having U-shaped or V-shaped structures.

In an embodiment, ends of the claws are inwardly congregated toward an axis of the clamping segment. A recess is defined on an outer periphery of the valve sewing segment. When the valve sewing segment is completely released, the recess is engaged with the inwardly congregated claws.

In an embodiment, when the valve sewing segment is completely released, the autologous valve leaflets are located between the claws and the valve sewing segment.

In an embodiment, the guiding device has a flexible string structure or a strip structure. In an embodiment, the guiding device includes a plurality of flexible strings.

In an embodiment, the guiding device is located between the positioning member and the valve sewing segment.

In an embodiment, the guiding device straddles over free edges of the autologous valve leaflets. In an embodiment, the autologous valve leaflets are straddled and lowered by the guiding device, ensuring that the coronary artery ostia cannot be blocked.

In an embodiment, a axial relative position between the valve sewing segment and the positioning member is limited by a length of the guiding device.

In an embodiment, the valve sewing segment and the positioning member are restricted and positioned at different positions in a delivery sheath.

In an embodiment, the slide connection structure is a hole. In an embodiment, the slide connection structure is integrated with the valve sawing segment. In an embodiment, the slide connection structure is located at a proximal end portion of the valve sewing segment.

In an embodiment, the connection sites between the guiding device and the anchoring segment are located on a distal end portion of the anchoring segment.

In an embodiment, a plurality of the slide connection structures is disposed on the valve sewing segment.

In an embodiment, the valve stent further includes an auxiliary guiding device. One end of the auxiliary guiding device is connected to the anchoring segment, and another end of the auxiliary guiding device is connected to the valve sewing segment.

In an embodiment, the released clamping segment is located at the autologous valve sinuses. At least a portion of the released anchoring segment is located in the blood vessel.

In an embodiment, a sealing member is disposed at a proximal end of the valve sewing segment. When the separately releasable aortic valve stent is implanted, the sealing member prevents the blood from passing through the gap between the valve sewing segment and the autologous tissue.

In an embodiment, the sealing member has a discontinuous strip structure. In an embodiment, when the separately releasable aortic valve stent is implanted, the lower portions of the claws are corresponding to the discontinuous regions of the sealing member.

In an embodiment, a coordination structure is disposed on a distal end of the anchoring segment. A connection structure is disposed on a proximal end of the valve sewing segment. The coordination structure and the connection structure are restrained to each other when being restricted and loaded in a delivery sheath.

In an embodiment, the connection structure is a rod. The coordination structure is a hole. When the valve stent is restricted and loaded in the delivery sheath, the connection structure is passed through the coordination structure. In an embodiment, a position-limiting hole is defined in the connection structure. When the valve stent is restricted and loaded in the delivery sheath, the connection structure is passed through the coordination structure, and a position-limiting wire is passed through the position-limiting hole.

In an embodiment, the connection structure is a loop. The coordination structure is a hole. When the valve stent is restricted and loaded in the delivery sheath, the connection structure is passed through the coordination structure, and a position-limiting wire is passed through the loop.

In an embodiment, a recess is defined on the connection structure. A protrusion is formed on the coordination structure. The recess and the protrusion are complementary to each other.

As compared to the traditional technology, the present application has the following advantages.

1. Different from the traditional technology, the guiding device is disposed between the positioning device and the main valve stent part (which includes the valve sewing segment and the prosthetic valve) in the present application. The guiding device has at least the following four main functions. 1) The valve sewing segment can slide to the specified position along the guiding device, and such movement manner can significantly increase the concentricity between the valve sewing segment and the positing member, avoiding the mutual interference and malposition therebetween in the process of the relative movement. 2) In the process of aligning and releasing the main valve stent part and the positioning member, the guiding device straddles over the free edges of the protogenetic autologous valve leaflets to effectively limit the movements of the free edges of the autologous valve leaflets. When the release is completed, the height of the free edges of the autologous valve leaflets can be automatically lowered, so that the blockage of the coronary artery ostia can be prevented, and the anchoring effect can be increased. 3) The controllable release of the positioning member can be achieved with the assist of the guiding device. 4) The guiding device can also limit the relative position between the main valve stent part and the positioning member, thus facilitating the operation of the doctor.

2. Different from the fixation manner in the traditional technology, in the present application, the clamping segment is firstly positioned at the autologous aortic sinuses after the release, and then the anchoring segment is at least partially located in the blood vessel after the release, adopting the ascending aorta for the fixation. Such design can ensure that the positioning member will not be detached after the release, and provide sufficient time for the subsequent release of the main valve stent part.

3. Due to the mutual restraint between the valve sewing segment and the positioning member, the controllable release of the positioning member can be achieved, thus preventing the influence on the implantation effect caused by the bounce of the positioning member from the delivery sheath in the release process, facilitating the control and the regulation of the angle and the position of the clamping segment, allowing the positioning member that has been completely released to be reloaded into the sheath, and decreasing the operation risk. As compared to the traditional technology which separately controls the main valve stent part and the positioning member, such mutual restraint can maximally reduce the size of the sheath.

4. Different from the traditional technology, the sealing member in the present application has a discontinuous strip structure. When the valve stent is implanted, the lower portions of the claws are corresponding to the discontinuous regions of the sealing member; that is, the continuous portions of the sealing member are corresponding to the junctions between the autologous valve leaflets. Such a specific partial blocking technique effectively decreases the diameter of the sheath while ensuring the effect of reducing the perivalvular leakage.

5. Different from the traditional technology, the engagement portions of the clamping segment and the valve sewing segment are complementary recess and protrusion. Such design allows the convenient alignment and fixation of the positioning member and the main valve stent part, facilitates the anchoring, and reduces the perivalvular leakage.

BRIEF DESCRIPTION OF THE DRAWINGS

To describe the technical solutions in the embodiments of the present application or in the traditional technology more clearly, the following briefly describes the accompanying drawings referred in the description of the embodiments. The accompanying drawings in the following description show merely some embodiments of the present application, and a person of ordinary skill in the art may derive other drawings from the provided accompanying drawings without creative efforts.

DETAILED DESCRIPTION

The technical solutions in the embodiments of the present application will be described clearly and completely in the following with reference to the accompanying drawings in the embodiments of the present application. Apparently, the described embodiments are merely some rather than all of the embodiments of the present application. All other embodiments obtained by one of ordinary skill in the art based on the embodiments of the present application without creative efforts shall fall within the protection scope of the present application.

Unless otherwise defined, all the technical and scientific terms used in this specification have the same meaning as commonly understood by one of ordinary skill in the art to which this application belongs. Additionally, the terms used in the specification of the present application are merely for describing the specific embodiments, and are not intended to limit the present application. As used herein, the term "and/or" includes any and all combinations of one or more of the associated listed items.

The distal end described in the present application refers to the end farther from the apex of the heart, and the proximal end described in the present application refers to the end nearer to the apex of the heart.

Example 1

Figure 1A:
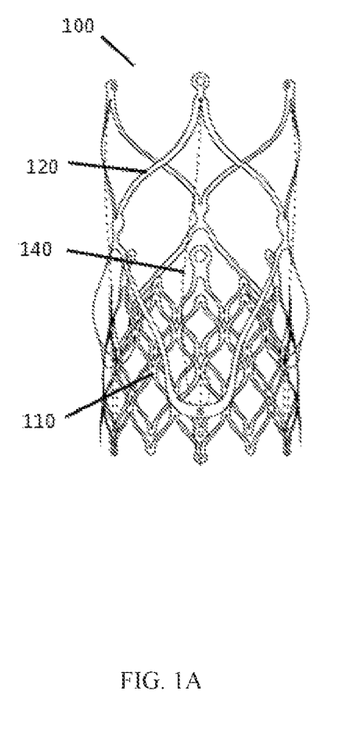
FIG. 1A and FIG. 1B are schematic views of an embodiment of the present application.
Figure 1B:
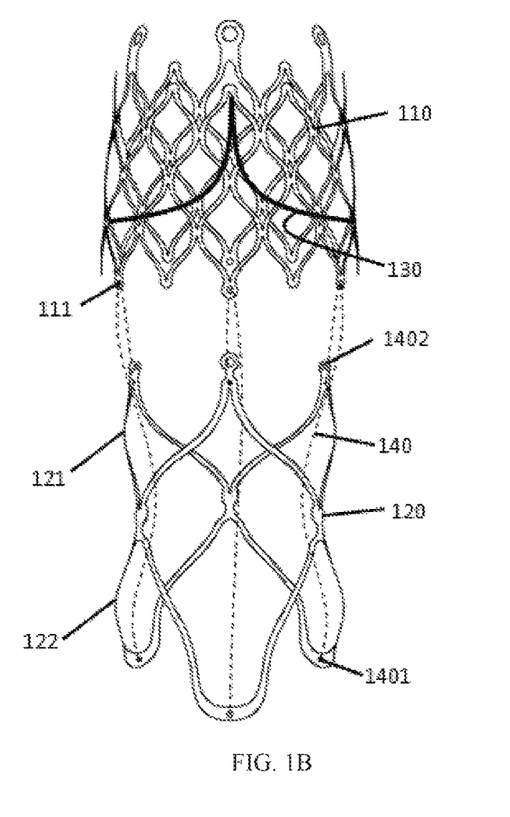
Figure 1C:
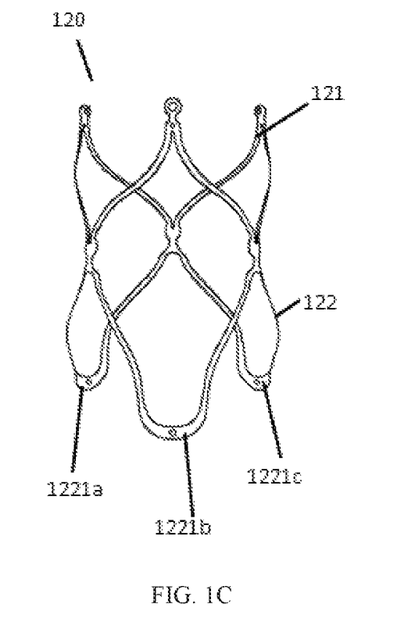
FIG. 1C is a schematic structural view of a positioning member in the present application.
Figure 1D:
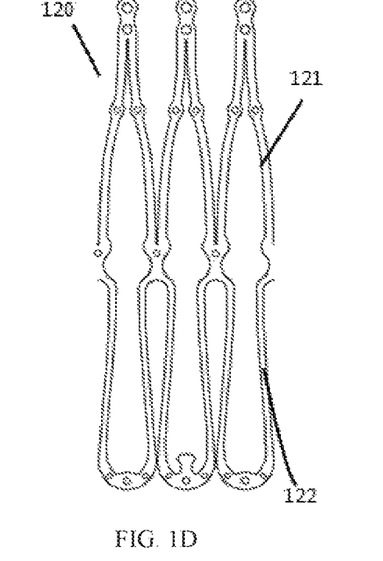
FIG. 1D and FIG. 1E are partial views of aortic valve stents in the present application.
Figure 1E:
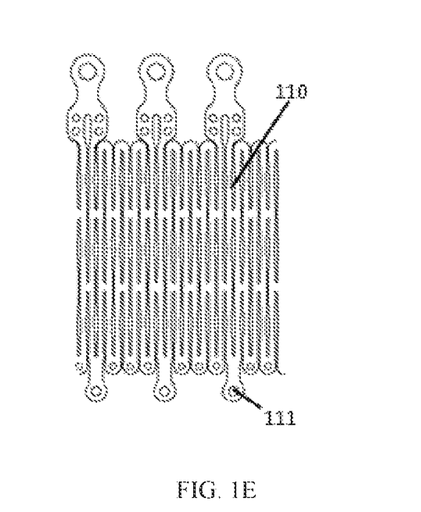

Referring to FIG. 1A to FIG. 1E, in an embodiment, a separately releasable aortic valve stent 100 includes a valve sewing segment 110, a positioning member 120, and a prosthetic valve 130. The prosthetic valve 130 is connected to the valve sewing segment 110. The valve sewing segment 110 and the positioning member 120 are two independent components and connected to each other via a guiding device 140, such that the valve sewing segment 110 and the positioning member 120 are positioned at different positions when restricted in a delivery sheath, thereby reducing the diameter of the delivery sheath. The positioning member 120 is released prior to the valve sewing segment 110. A slide connection structure 111 is disposed on the valve sewing segment 110. One end of the guiding device 140 is connected to the positioning member 120, and the other end of the guiding device 140 is passed through the slide connection structure 111 and then connected to the positioning member 120. The valve sewing segment 110 is slidable along the guiding device 140. In an embodiment, the positioning member 120 includes an anchoring segment 121 and a clamping segment 122. The clamping segment 122 is located at a proximal end of the anchoring segment 121. A distal end of the clamping segment 122 is connected to the proximal end of the anchoring segment 121. In this embodiment, the clamping segment 122 is integrated with the anchoring segment 121. One end 1401 of the guiding device 140 is connected to the clamping segment 122, and the other end 1402 of the guiding device 140 is passed through the slide connection structure 111 and then connected to the anchoring segment 121. The valve sewing segment 110 is slidable along the guiding device 140. The clamping segment 122 has three claws 1221 (1221a, 1221b, 1221c) which are circumferentially disposed and uniformly spaced. The claws have U-shaped or V-shaped structures and are configured to engage with physiological structures of the three aortic sinuses. After the release, the claws reach the backs of the autologous valve leaflets and the bottoms of the aortic sinuses to accomplish the positioning. The guiding device 140 has a flexible string structure. In an embodiment, the guiding device 140 includes three flexible strings. In another embodiment, more flexible strings can be used to connect the valve sewing segment 110 and the positioning member 120, so as to achieve a more stable positioning. It should be noted that more flexible strings may increase the delivery resistance. FIG. 1D shows a portion of the positioning member 120. FIG. 1E shows a portion of the valve sewing segment 110.

Figure 2A:
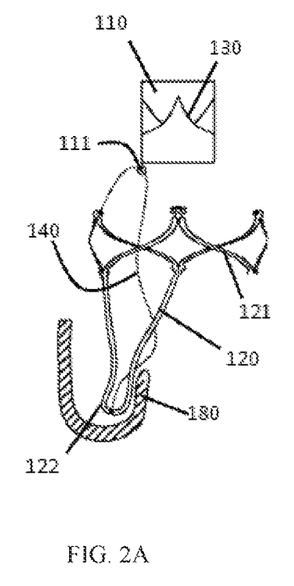
FIG. 2A to FIG. 2C are schematic views showing the movement trajectories of a valve sewing segment, a positioning member, and a guiding device in the present application.
Figure 2B:
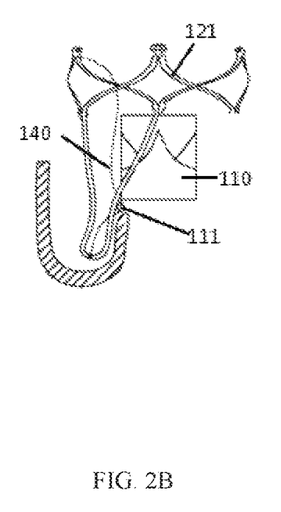
Figure 2C:
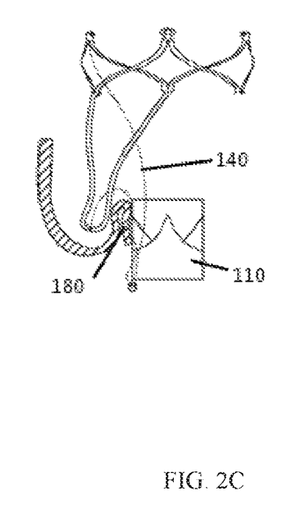
Figure 2D:
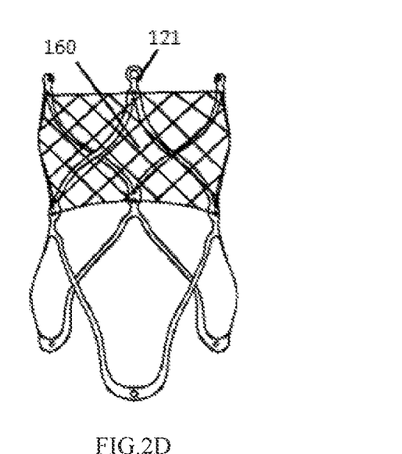
FIG. 2D is a schematic view of an embodiment of the positioning member in the present application.

As shown in FIG. 2A to 2C, in an embodiment, the guiding device 140 is located between the positioning member 120 and the valve sewing segment 110. As such, the damage in the slide caused by the guiding device 140 to the prosthetic valve 130 sewed onto the valve sewing segment 110 can be maximally prevented. Moreover, it is possible to lower the free edges of the autologous valve leaflets in the subsequent process. Specifically, the proximal end portion of the valve sewing segment 110 is provided with three slide connection structures 111 which are holes. In an embodiment, the slide connection structures 111 are integrated with the valve sewing segment 110. When the valve sewing segment 110 is completely released, the guiding device 140 straddles over the free edges of the autologous valve leaflets 180. The axial relative position between the valve sewing segment 110 and the positioning member 120 is limited by the length of the guiding device 140. In fact, by adjusting the length of the guiding device 140, when the position of the valve sewing segment 110 is limited at the position of the valve annulus of the patient, the autologous valve leaflets 180 are straddled and are lowered by the guiding device 140, thus ensuring that the coronary artery ostia will not be blocked. Moreover, as shown in FIG. 2D, the anchoring segment 121 has a mesh structure, and the surface of the anchoring segment 121 is coated by a film or a fabric 160 to avoid the blood vessel dissection. In another embodiment, the anchoring segment 121 has a wavy structure (not shown). The connecting site between the guiding device 140 and the anchoring segment 121 is located at a distal end portion of the anchoring segment 121. The valve sewing segment 110 and the positioning member 120 are compressed and positioned at different positions in the delivery sheath. The guiding device 140 can assist the released positioning member 120 to be reloaded into the sheath, especially when the vast majority of the positioning member 120 has been released. The doctor can draw back the positioning member 120 and release the positioning member 120 again depending on the positioning effect, thus significantly increasing the success rate of operation. In view of the above, different from the traditional technology, the guiding device in the present application has at least the following four main functions: 1. The valve sewing segment can slide to the specified position along the guiding device, and such movement manner can significantly increase the concentricity between the valve sewing segment and the positing member, avoiding the mutual interference and malposition therebetween in the process of the relative movement. 2. In the process of aligning and releasing the main valve stent part and the positioning member, the guiding device straddles over the free edges of the protogenetic autologous valve leaflets to effectively limit the movements of the free edges of the autologous valve leaflets. When the release is completed, the height of the free edges of the autologous valve leaflets can be automatically lowered, so that the blockage of the coronary artery ostia can be prevented, and the anchoring effect can be increased. 3. The controllable release of the positioning member can be achieved with the assist of the guiding device. 4. The guiding device can also limit the relative position between the main valve stent part and the positioning member, thus facilitating the operation of the doctor.

Figures 3A, 3B, 3C:
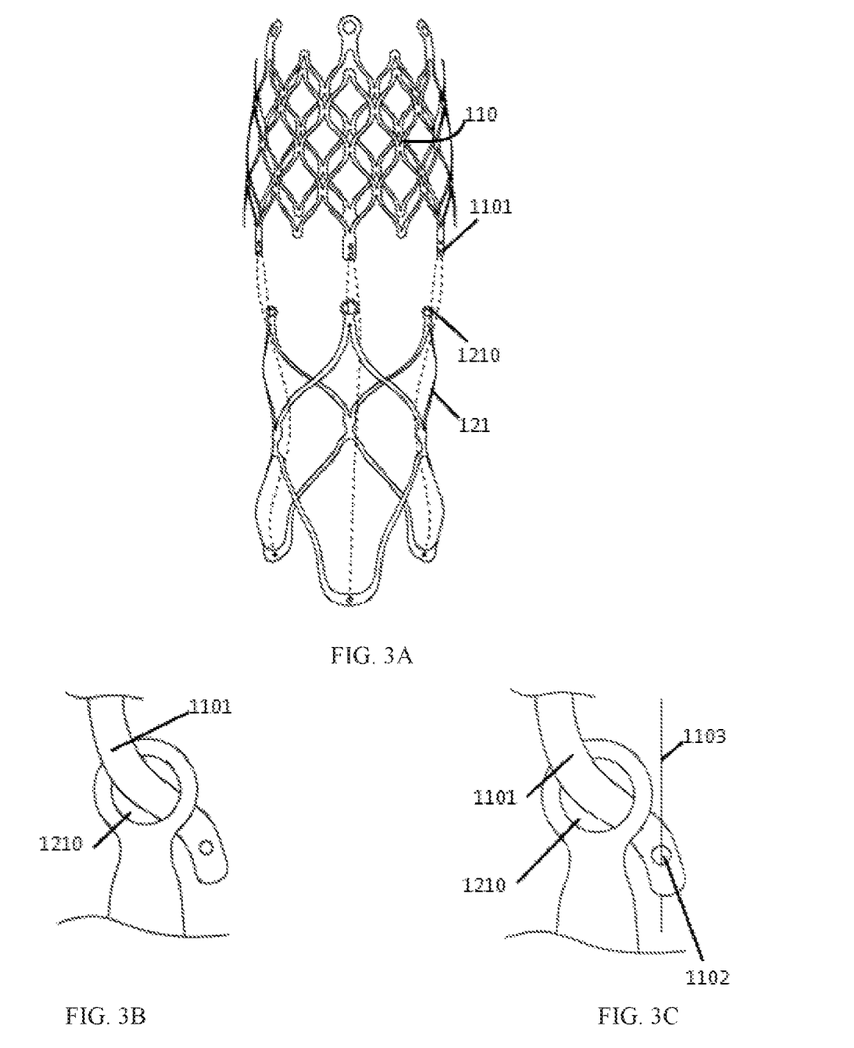
FIG. 3A to FIG. 3D are schematic views of a coordination structure and a connection structure in the present application.
Figure 3D:
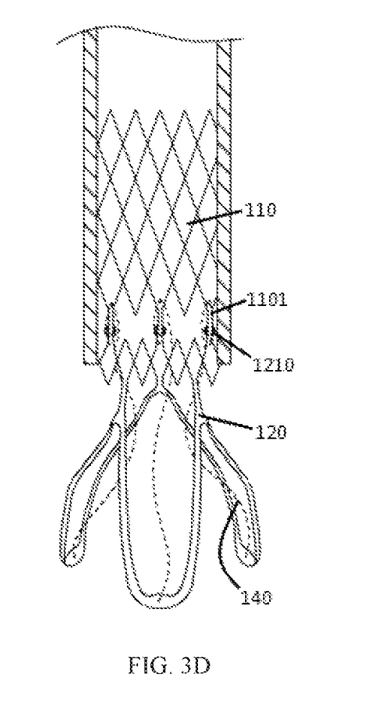
Figure 3E:
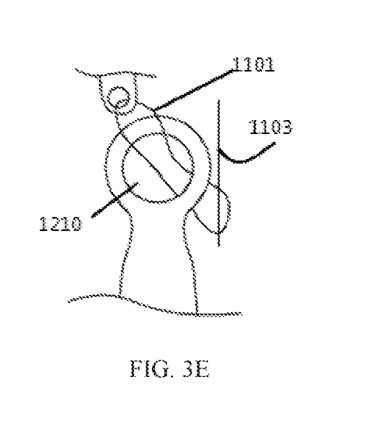
FIG. 3E is a schematic view of an embodiment of the coordination structure and the connection structure in the present application.

As shown in FIG. 3A, the distal end of the anchoring segment 121 is provided with a coordination structure 1210. The proximal end of the valve sewing segment 110 is provided with a connection structure 1101. When being restricted and loaded in the delivery sheath, the connection structure 1101 and the coordination structure 1210 are restrained to each other. As shown in FIG. 3B, in an embodiment, the connection structure 1101 is a rod, and the coordination structure 1210 is a hole. When the valve stent 100 is restricted and loaded in the delivery sheath, the connection structure 1101 is passed through the coordination structure 1210. As shown in FIG. 3C and FIG. 3D, a position-limiting hole 1102 is defined in the connection structure 1101. When the valve stent 100 is restricted and loaded in the delivery sheath, the connection structure 1101 is passed through the coordination structure 1210, and then a position-limiting wire 1103 is passed through the position-limiting hole 1102. The connection structure 1101 can be removed from the coordination structure 1210 only when the position-limiting wire 1103 is pulled out. Due to the mutual restraint between the valve sewing segment 110 and the positioning member 120, the controllable release of the positioning member 120 can be achieved, thus preventing the influence on the implantation effect caused by the bounce of the positioning member 120 from the delivery sheath in the release process, facilitating the control and the regulation of the angle and the position of the clamping segment 122, allowing the positioning member 120 that has been completely released to be reloaded into the sheath, and decreasing the operation risk. As compared to the traditional technology which separately controls the main valve stent part and the positioning member, such mutual restraint can maximally reduce the size of the sheath. In another embodiment, as shown in FIG. 3E, the connection structure 1101 is a loop, and the coordination structure 1210 is a hole. When the valve stent 100 is restricted and loaded in the delivery sheath, the connection structure 1101 is passed through the coordination structure 1210, and then the position-limiting wire 1103 is passed through the connection structure 1101.

To better illustrate the present embodiment, the operation steps of delivering and releasing the valve stent 100 is described as follows.

Figure 4A:
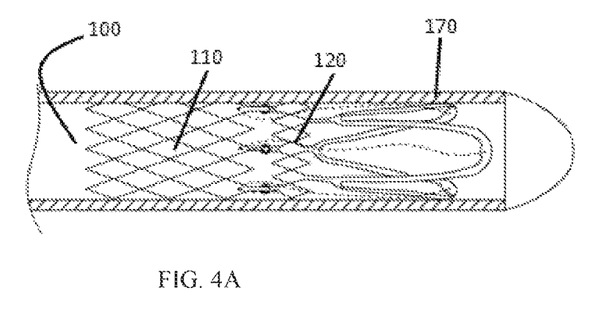
FIG. 4A to FIG. 4L are schematic views of operation steps in the present application.
Figure 4B:
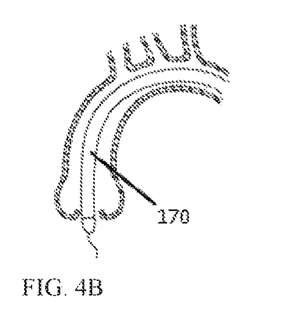

(1) As shown in FIG. 4A and FIG. 4B, the valve stent 100 is compressed and loaded into the delivery sheath 170. The valve sewing segment 110 is located at the distal end of the positioning member 120. With the assistance of an imaging instrument, the implant is delivered to the lesion site of the patient via a transfermoral route or the like route.

Figure 4C:
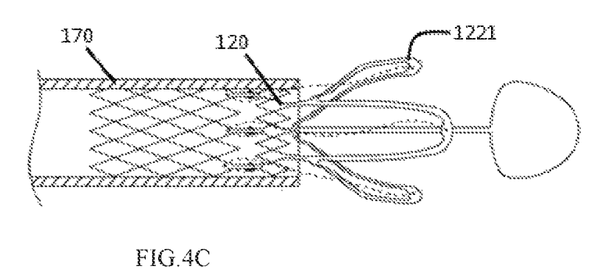
Figure 4D:
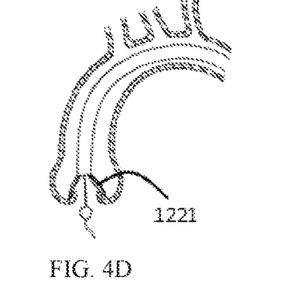

(2) As shown in FIG. 4C and FIG. 4D, the clamping segment 122 is gradually released until all of the claws 1221 are opened at an angle. The released clamping segment 122 is located at the autologous valve sinuses. At this time, the anchoring segment 121 is still compressed in the delivery sheath.

Figure 4E:
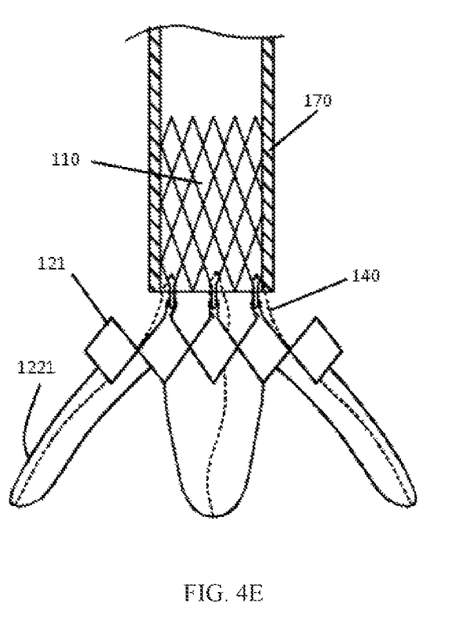
Figure 4F:
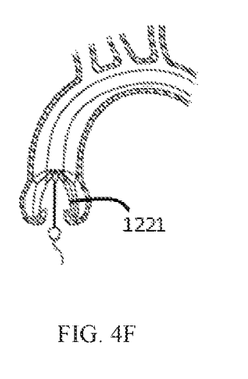

(3) As shown in FIG. 4E and FIG. 4F, the angles and the positions of the claws 1221 are adjusted. After the claws 1221 reach the backs of the autologous valve leaflets and the bottoms of the aortic valve sinuses, the anchoring segment 121 is gradually released. At least a portion of the released anchoring segment 121 is located in the blood vessel to provide the anchoring force. Due to the mutual restraint between the valve sewing segment 110 and the positioning member 120, the anchoring segment 121 will not bounce. Moreover, due to the fixation manner utilizing the ascending aorta, the completely released positioning member 120 will not be displaced or removed under the blood current flush. Thus, sufficient time can be provided for the subsequent release of the main valve stent part. More importantly, if the position of the positioning member 120 is unsatisfactory, with the assist of the guiding device 140, the positioning member 120 can be reloaded into the sheath, and released again or removed from the body, thereby significantly decreasing the operation risk.

Figure 4G:
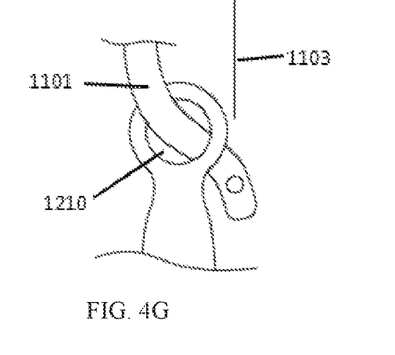
Figure 4H:
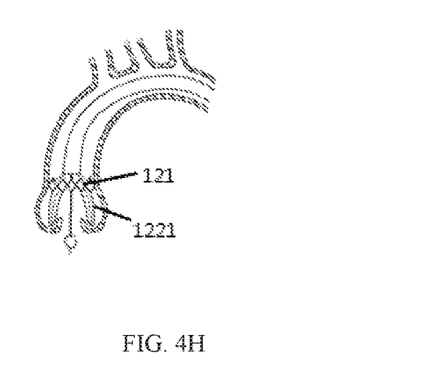

(4) As shown in FIG. 4G and FIG. 4H, after the position is assured, the position-limiting wire 1103 is pulled out, the connection structure 1101 is removed from the coordination structure 1210, and the anchoring segment 121 is completely released and anchored into the ascending aorta.

Figure 4I:
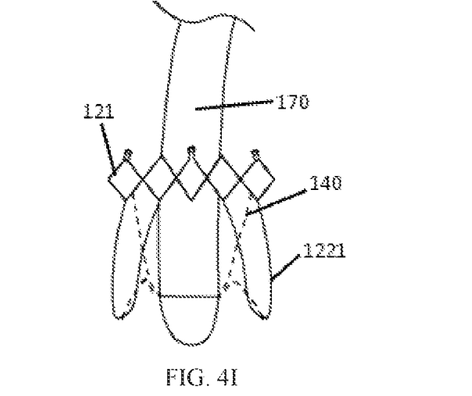
Figure 4J:
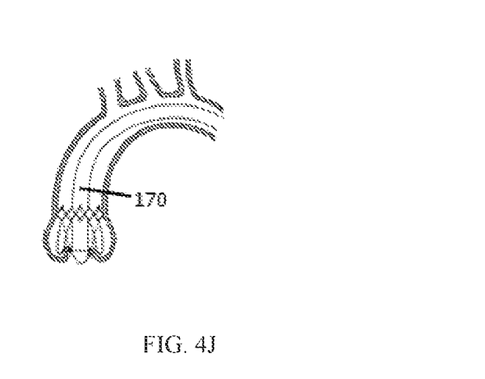

(5) As shown in FIG. 4I and FIG. 4J, the guiding tip is re-located onto the sheath, so that the delivery sheath 170 with the valve sewing segment 110 compressed therein can better pass through the autologous valve leaflets. The sheath is pushed along the guiding device 140 until the position of the sheath is limited by the length of the guiding device 140. At this time, the autologous valve leaflets 180 are straddled and lowered by the guiding device 140.

Figure 4K:
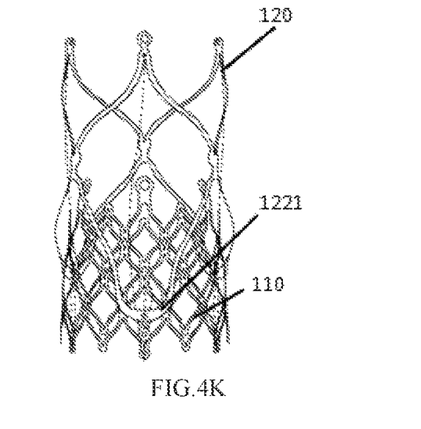
Figure 4L:
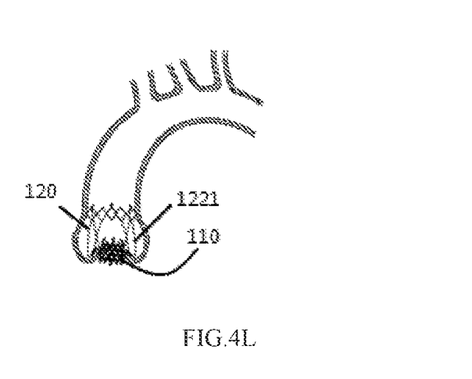

(6) As shown in FIG. 4K and FIG. 4L, the valve sewing segment 110 is gradually released until it is completely released. When the valve sewing segment 110 is completely released, the autologous valve leaflets 180 are maintained in the lowered state and located between the claws 1221 and the valve sewing segment 110.

(7) The delivery sheath is removed.

The valve stent 100 can also be delivered and released via the heat apex route, the atrial septostomy, or other routes. The operation steps are similar to those described above and will not be repeated again.

Example 2

Figure 5A:
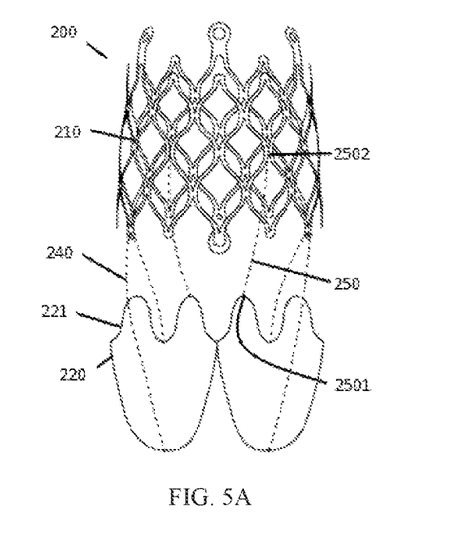
FIG. 5A and FIG. 5B are schematic views of another embodiment in the present application.

Referring to FIG. 5A, in another embodiment, a separately releasable aortic valve stent 200 includes a valve sewing segment 210, a positioning member 220, and a prosthetic valve (not shown). The prosthetic valve is connected to the valve sewing segment 210. The valve sewing segment 210 and the positioning member 220 are two independent components and connected to each other via a guiding device 240. The guiding device 240 has a strip structure. Example 2 is distinguished with Example 1 in that the valve stent 200 further includes an auxiliary guiding device 250. Specifically, the auxiliary guiding device 250 is strings. One end 2501 of the auxiliary guiding device 250 is connected to the anchoring segment 221, and the other end 2502 of the auxiliary guiding device 250 is connected to the valve sewing segment 210. The auxiliary guiding device 250 in combination with the guiding device 240 makes the valve sewing segment 210 and the positioning member 220 be more stably positioned. Since the two ends of the auxiliary guiding device 250 are not connected to the same positions as those of the guiding device 240, the length of the auxiliary guiding device 250 should be well-designed according to the length of the guiding device 240.

Figure 5B:
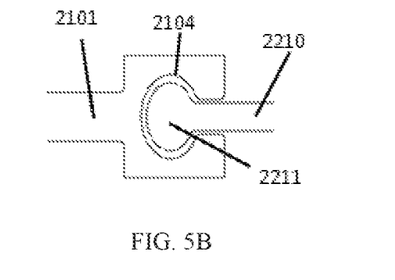

The distal end of the anchoring segment 221 is provided with a coordination structure 2210. The proximal end of the valve sewing segment 210 is provided with a connection structure 2101. When being restricted and loaded in the delivery sheath, the connection structure 2101 and the coordination structure 2210 are restrained to each other. In an embodiment, as shown in FIG. 5B, a recess 2104 is defined on the connection structure 2101, a protrusion 2211 is defined on the coordination structure 2210, and the recess 2104 and the protrusion 2211 are complementary to each other.

Example 3

Figure 6A:
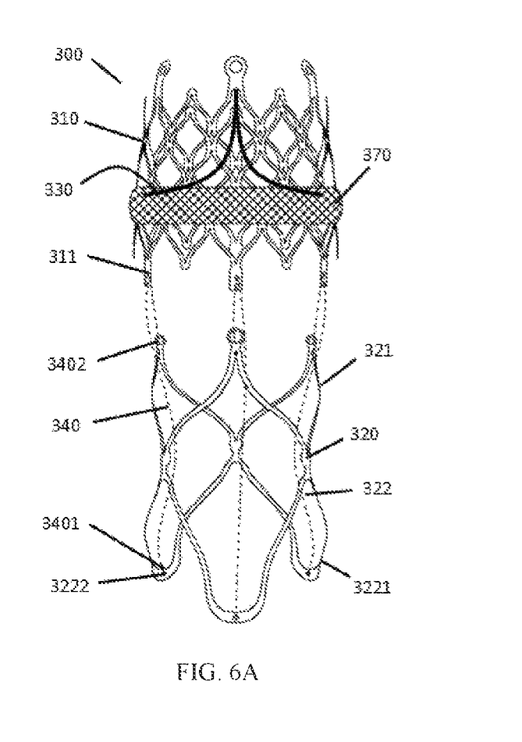
FIG. 6A is a schematic view of another embodiment in the present application.
Figure 6B:
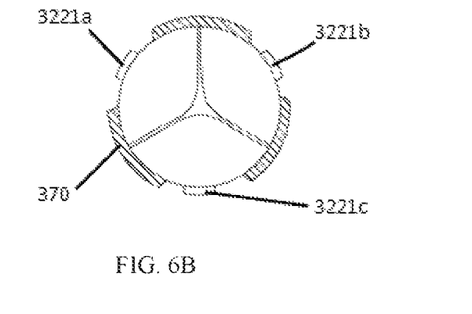
FIG. 6B is a schematic view of an embodiment of a sealing member.

As shown in FIG. 6A, in another embodiment, a separately releasable aortic valve stent 300 includes a valve sewing segment 310, a positioning member 320, and a prosthetic valve 330. The prosthetic valve 330 is connected to the valve sewing segment 310. The valve sewing segment 310 and the positioning member 320 are two independent components and connected to each other via a guiding device 340. The positioning member 320 is released prior to the valve sewing segment 310. The positioning member 320 includes an anchoring segment 321 and a clamping segment 322. The clamping segment 322 has three claws 3221. A slide connection structure 311 is disposed on the valve sewing segment 310. One end 3401 of the guiding device 340 is connected to the holes on the bottom ends of the claws 3221, and the other end 3402 of the guiding device 140 is passed through the slide connection structure 311 and then connected to the anchoring segment 321. The valve sewing segment 310 is slidable along the guiding device 340. Example 3 is distinguished with the aforementioned examples in that a sealing member 370 is disposed at the proximal end of the valve sewing segment 310. When the valve stent 300 is implanted, the sealing member 370 prevents the blood from passing through the gap between the valve sewing segment and the autologous tissue. Since the autologous valve leaflets have the auxiliary leakage-proof effect, the regurgitation tends to occur at the junctions between the autologous valve leaflets. In an embodiment, as shown in FIG. 6B, the sealing member 370 has a discontinuous strip structure. When the valve stent 300 is implanted, the lower portions of the claws 3221 (3221a, 3221b, 3221c) are corresponding to the discontinuous regions of the sealing member 370; that is, the continuous portions of the sealing member 370 are corresponding to the junctions between the autologous valve leaflets. Such a well-designed partial blocking technique effectively decreases the diameter of the sheath while ensuring the effect of reducing the perivalvular leakage.

Figure 6C:
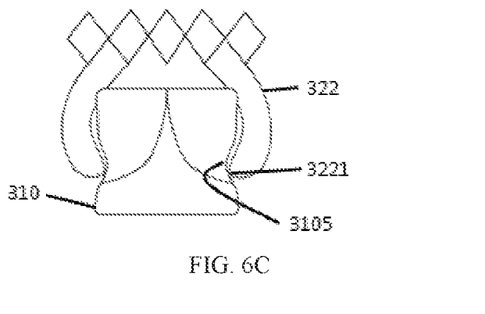
FIG. 6C is a schematic view of another embodiment of the valve sewing segment and the positioning member in the present application.

As show in FIG. 6C, the ends of the claws 3221 have a structure congregated inwardly toward an axis of the clamping segment 322. In an embodiment, a recess 3105 is defined on the outer periphery of the valve sewing segment 310. When the valve sewing segment 310 is completely released, the recess 3105 is engaged with the inwardly congregated structure of the claws 3221. Such design allows the convenient alignment and fixation of the positioning member and the main valve stent part, facilitates the anchoring, and reduces the perivalvular leakage.

Figure 6D:
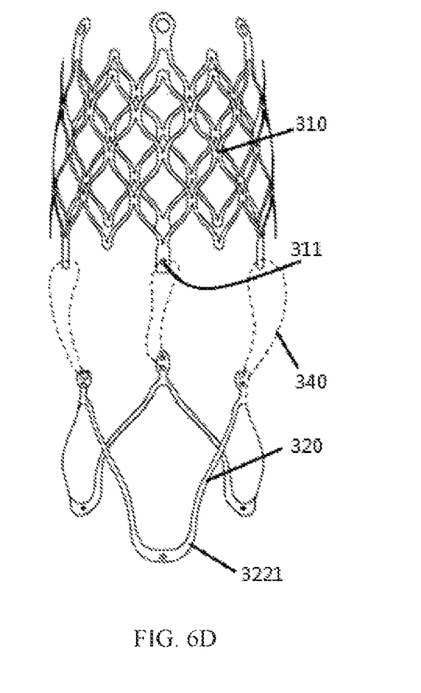
FIG. 6D is a schematic view of yet another embodiment in the present application.

As shown in FIG. 6D, in another embodiment, a slide connection structure 311 is disposed on the valve sewing segment 310. The connection sites between the guiding device 340 and the positioning member 320 are staggered with the claws 3221 in the axial direction. The valve sewing segment 310 is slidable along with the guiding device 340.

The technical features of the above-described embodiments may be arbitrarily combined. In order to make the description simple, not all possible combinations of the technical features in the above embodiments are described. However, as long as there is no contradiction in the combination of these technical features, the combinations should be in the scope of the present application.

What described above are only several embodiments of the present application, and these embodiments are specific and detailed, but not intended to limit the scope of the present application. It should be understood by one ordinary skill in the art that various modifications and improvements can be made without departing from the conception of the present application, and all fall within the protection scope of the present application. Therefore, the patent protection scope of the present application is defined by the appended claims.

What is claimed is:

1. A separately releasable aortic valve stent, comprising:
   a valve sewing segment,
   a positioning member,
   a guiding device, and
   a prosthetic valve,
   wherein the valve sewing segment is a stent segment of the separately releasable aortic valve stent, the positioning member is also an anchoring member, the prosthetic valve is sewed to the valve sewing segment, the valve sewing segment and the positioning member are two independent components and connected to each other via the guiding device, the positioning member is able to be released prior to the valve sewing segment, the valve sewing segment comprises a slide connection structure, one end of the guiding device is connected to the positioning member, another end of the guiding device passed through the slide connection structure is connected to the positioning member, and the valve sewing segment is slidable along the guiding device,
   wherein the guiding device is configured to allow autologous valve leaflets of a patient to be straddled and lowered by the guiding device when the valve sewing segment is completely released and the position of the valve sewing segment is limited at a position of a valve annulus of the patient,
   wherein the positioning member comprises an anchoring segment and a clamping segment connected to the anchoring segment, one end of the guiding device is directly connected to the clamping segment, another end of the guiding device passed through the slide connection structure is directly connected to the anchoring segment, and the valve sewing segment is slidable along the guiding device via the slide connection structure.

2. The separately releasable aortic valve stent of claim 1, wherein the clamping segment has claws, ends of the claws are inwardly congregated toward an axis of the clamping segment, and a recess is defined on an outer periphery of the valve sewing segment; when the valve sewing segment is completely released, the recess is engaged with the inwardly congregated claws.

3. The separately releasable aortic valve stent of claim 1, wherein the guiding device has a flexible string structure or a strip structure.

4. The separately releasable aortic valve stent of claim 1, wherein the guiding device is located between the positioning member and the valve sewing segment.

5. The separately releasable aortic valve stent of claim 1, wherein a relative position between the valve sewing segment and the positioning member is limited by a length of the guiding device.

6. The separately releasable aortic valve stent of claim 1, wherein the valve sewing segment and the positioning member are restricted and positioned at different positions in a delivery sheath.

7. The separately releasable aortic valve stent of claim 1, wherein the slide connection structure is located at a proximal end portion of the valve sewing segment, and connection sites between the guiding device and the anchoring segment are located on a distal end portion of the anchoring segment.

8. The separately releasable aortic valve stent of claim 1, further comprising an auxiliary guiding device, one end of the auxiliary guiding device is connected to the anchoring segment, and another end of the auxiliary guiding device is connected to the valve sewing segment.

9. The separately releasable aortic valve stent of claim 1, wherein a sealing member is disposed at a proximal end of the valve sewing segment.

10. The separately releasable aortic valve stent of claim 9, wherein the sealing member has a discontinuous strip structure.

11. The separately releasable aortic valve stent of claim 1, wherein a coordination structure is disposed on a distal end of the anchoring segment, a connection structure is disposed on a proximal end of the valve sewing segment, and the coordination structure and the connection structure are restrained to each other when being restricted and loaded in a delivery sheath.

12. The separately releasable aortic valve stent of claim 11, wherein the connection structure is a rod, the coordination structure is a hole, and when the separately releasable aortic valve stent is restricted and loaded in the delivery sheath, the connection structure is passed through the coordination structure.

13. The separately releasable aortic valve stent of claim 12, wherein a position-limiting hole is defined in the connection structure, and when the separately releasable aortic valve stent is restricted and loaded in the delivery sheath, the connection structure is passed through the coordination structure, and a position-limiting wire is passed through the position-limiting hole.

14. The separately releasable aortic valve stent of claim 11, wherein the connection structure is a loop, the coordination structure is a hole, and when the separately releasable aortic valve stent is restricted and loaded in the delivery sheath, the connection structure is passed through the coordination structure, and a position-limiting wire is passed through the loop.

15. The separately releasable aortic valve stent of claim 1, wherein the clamping segment has three claws which are circumferentially disposed and uniformly spaced and are configured to engage with physiological structures of the three aortic sinuses.

16. The separately releasable aortic valve stent of claim 1, wherein the clamping segment is located at a proximal end of the anchoring segment, and integrated with the anchoring segment.

17. The separately releasable aortic valve stent of claim 1, wherein the guiding device comprises a plurality of flexible strings.

* * * * *